US00PP30856P2

(12) United States Plant Patent
Korlipara

(10) Patent No.: US PP30,856 P2
(45) Date of Patent: Aug. 27, 2019

(54) *ECHINACEA* PLANT NAMED 'TNECHKW'

(50) Latin Name: ***Echinacea* spp.**
Varietal Denomination: TNECHKW

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/998,107

(22) Filed: Jun. 29, 2018

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 6/1448; A01H 5/02
See application file for complete search history.

*Primary Examiner* — Keith O. Robinson
(74) *Attorney, Agent, or Firm* — Klarquist Sparkman, LLP

(57) ABSTRACT

A new and distinct *Echinacea* plant named 'TNECHKW' characterized by an amazing number of large inflorescences starting in the first season, very long bloom time with excellent rebloom, a very upright, very compact habit, white ray florets surrounding green cones, ray florets held horizontally when young then dropping slightly, strong upright stems, and excellent vigor.

1 Drawing Sheet

Botanical denomination: *Echinacea* spp.
Variety designation: 'TNECHKW'.
Trademark designation: Kismet™ White.

BACKGROUND OF THE INVENTION

The present invention relates to a new and distinct cultivar of *Echinacea* and given the cultivar name 'TNECHKW'. *Echinacea* is in the family Asteraceae. The new cultivar is part of a planned breeding program for a container and edging series with compact habits and profuse inflorescences. The exact parents of this selection are unknown, unnamed, proprietary interspecific hybrids bred from *Echinacea paradoxa, Echinacea purpurea,* and *Echinacea tennesseensis.*

Compared to *Echinacea* 'Mediation White' (U.S. Plant Pat. No. 27,015), the new cultivar is shorter.

Compared to *Echinacea purpurea* 'Purity' (U.S. Plant Pat. No. 19,441), the new cultivar is shorter, with narrower leaves, more crowns from the base, produces more flowers earlier, and has flowers with orange cones rather than green.

This new *Echinacea* cultivar is uniquely distinguished by:

1. an amazing number of large inflorescences starting in the first season,
2. very long bloom time with excellent rebloom,
3. very upright, very compact habit,
4. white ray florets surrounding green cones,
5. ray florets held horizontally when young then dropping slightly,
6. strong upright stems, and
7. excellent vigor.

This new cultivar has been reproduced only by asexual propagation (cuttings and tissue culture using shoot tips). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows an eight-month-old *Echinacea* 'TNECHKW' in flower growing in the trial field in full sun in mid-August in Canby, Oreg.

FIG. 2 shows a two-year-old *Echinacea* 'TNECHKW' in full bloom in late July in the trial field in full sun in Canby, Oreg.

DETAILED PLANT DESCRIPTION

The following is a detailed description of the new *Echinacea* cultivar based on observations of 7-month-old specimens growing in the trial bed in full sun in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on The *Royal Horticultural Society Colour Chart,* 5$^{th}$ edition, 2007.

Plant:

*Type.*—Herbaceous perennial.
*Hardiness.*—USDA Zones 4 to 9.
*Size.*—Grows to 48 cm wide and 39 cm tall to top of inflorescences.
*Form.*—Basal clump, with 9 to 11 stems from the base.
*Vigor.*—Excellent.

*Roots*.—Fibrous, with many downward growing and few laterals, ivory in color, Yellow White 158D, roots develop easily from cuttings from the crown.

Leaf (basal): Simple, lanceolate, blade grows to 17 cm long and 4.3 cm wide, margins sparsely serrate, apex acuminate, base attenuate, venation pinnate, both sides strigose, 137A with veins 145C on topside, 147B with veins 147C on bottom side; petiole clasping, to 8 cm long and 3 mm wide, strigose, 147C.

Leaf (stem):

*Type*.—Simple.

*Shape*.—Lanceolate.

*Arrangement*.—Alternate.

*Blade size*.—Grows to 13.5 cm long and 5.5 cm wide.

*Margins*.—Entire to slightly undulate.

*Apex*.—Acuminate.

*Base*.—Attenuate.

*Surface texture*.—Strigose on both sides.

*Variegation*.—Absent.

*Rugosity*.—Absent.

*Venation*.—Pinnate, Yellow Green 145C on both sides.

*Color*.—Topside Yellow Green 147A, bottom side closest to Yellow Green 147B.

*Petiole description*.—Clasping, grows to 10.5 cm long and 4 mm wide, scabrous, narrow leafy edges, topside and bottom side Yellow Green 147C.

Inflorescence:

*Type*.—Composite on terminal stalked heads, daisy.

*Flowering stem*.—Grows to 32 cm tall from the base of the plant to the terminal inflorescence; branched with 1 to 6 inflorescences per stem; diameter growing to 10 mm wide near the inflorescence; strigose; Yellow Green 147C mottled with Yellow Green 147B.

*Flowering stem strength*.—Strong.

*Size*.—Grows to 10.5 cm wide and 4.5 cm deep as disc enlarges.

*Form*.—Ray florets held horizontally, mature disc is conic.

*Immature inflorescence* (*bud*).—3 cm wide and 2.5 cm deep, ray florets held upright and rolled up so only the back color shows, Yellow Green 145B, disc color Yellow Green 144A.

*Ray florets*.—Without pistil or stamen, 19 to 25 in number, grow to 42 mm long and 12 mm wide, oblanceolate to narrowly elliptic with the tip two-to-three-toothed (each acute), entire margins, base attenuate, glabrous on both sides; fully open florets topside closest to White NN155A, bottom side White NN155A tinted Yellow Green 149D on tip and base; attitude of ray florets at origin, semi-drooping; twisting of the ray floret, absent.

*Disc*.—Medium sized, flat becoming conic, becoming 39 mm deep and 45 mm wide with maturity, Yellow Green 144A in background with bracts Yellow 13A.

*Disc florets*.—To about 400 in number, each with 1 pistil and 4 stamen, grow to 11 mm long and 3 mm wide, each with one persistent, very stiff linear bract (16 mm long and 3 mm wide with the top 2 mm Yellow 13A blending to 7 mm Yellow Green 144A to 7 mm of White NN155A on bottom); corolla 5 mm long and 2 mm wide, tubular, 5 lobed, glabrous and glossy, Green 137A; pistil 10 mm long, ovary 3 mm long, White NN155D with top Yellow Green 144A, style 5 mm long and Yellow Green 145C, 2-branched stigma spreading 2 mm wide, Greyed Brown N199A on top half; stamen 6 mm long, filaments 3 mm long and White 155A, anthers 3 mm long and Brown 200A, pollen Yellow Orange 21A.

*Involucral bracts*.—In 4 leafy series, area grows to 40 mm wide and 10 mm deep, lobes lanceolate in shape, reflexed, grow to 10 mm long and 3 mm wide, both sides Yellow Green 146A, margins strigose, tip acute, strigose on both sides.

*Receptacle*.—Grows to 18 mm wide and 22 mm deep, White NN155C.

*Bloom period*.—June through October in Canby, Oreg.

*Fragrance*.—Floral, honey.

*Pollen*.—Moderate to abundant.

*Lastingness*.—Each inflorescence lasts about two weeks in Canby, Oreg.

Seeds: 3 mm long and 2.5 mm wide, oval, Brown 200C.

*Fertility*.—Medium.

Disease and pests: No pests or diseases have been observed on plants grown under commercial conditions in Canby, Oreg. No resistances are known.

I claim:

1. A new and distinct *Echinacea* plant as herein illustrated and described.

* * * * *

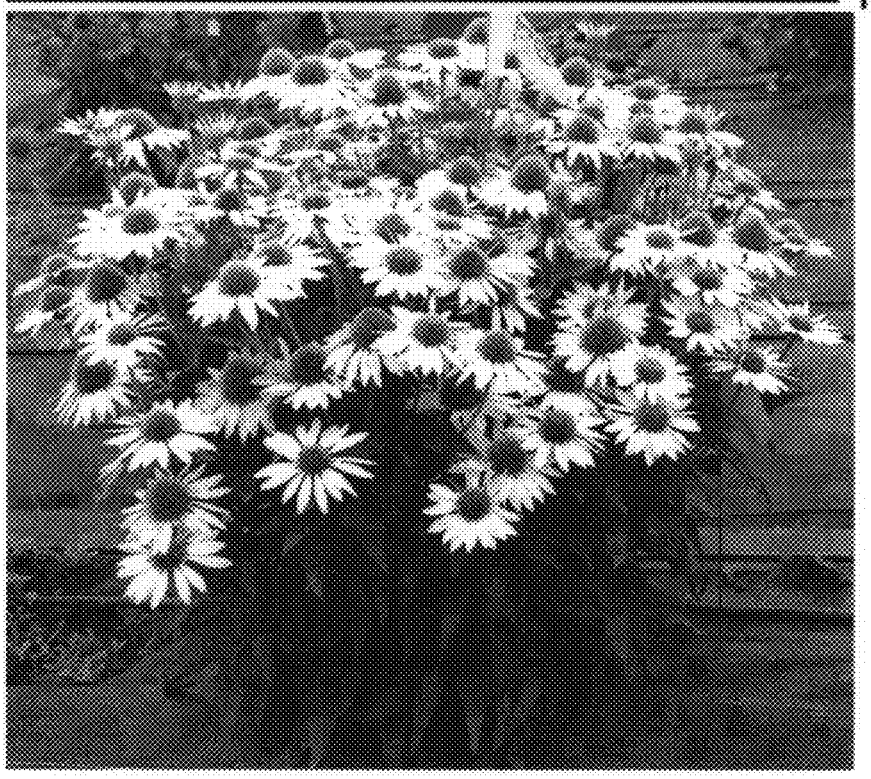

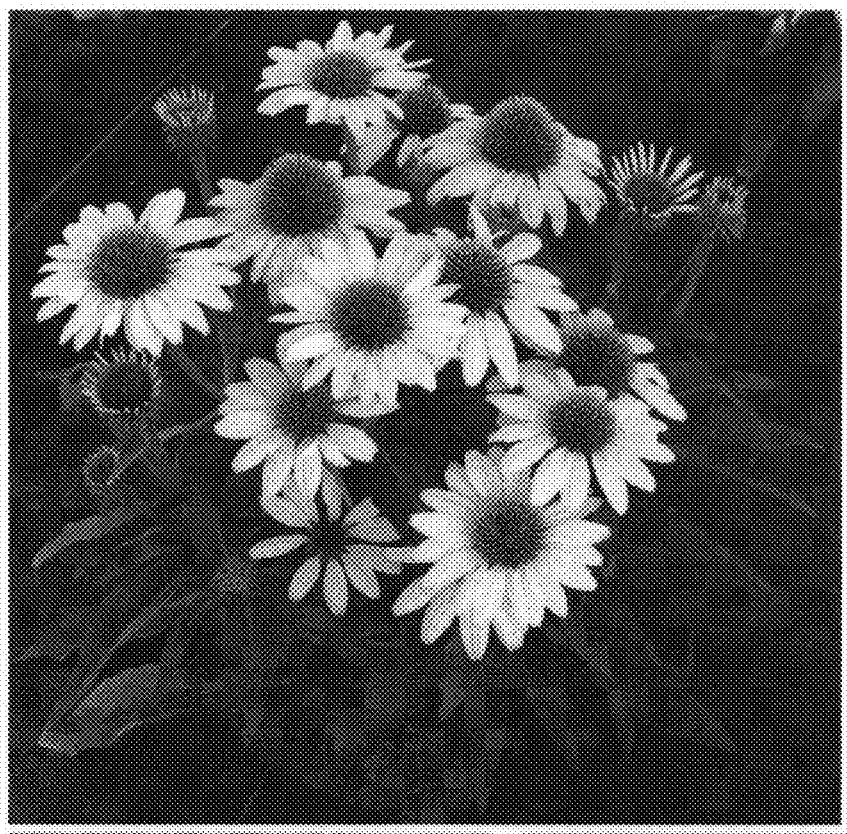
FIG.1 Above
FIG. 2 Below